United States Patent [19]

Ghahramani

[11] 4,225,778
[45] Sep. 30, 1980

[54] FLOW DETECTION SYSTEM

[75] Inventor: Iraj Ghahramani, Los Angeles, Calif.

[73] Assignee: International Telephone and Telegraph Corporation, New York, N.Y.

[21] Appl. No.: 32,557

[22] Filed: Apr. 23, 1979

[51] Int. Cl.³ .............................................. G06M 3/08
[52] U.S. Cl. ............................ 235/92 FL; 73/61.1 R; 73/861.04
[58] Field of Search ...................... 235/92 FL, 92 CP; 73/194 R, 61.1 R; 364/465, 510

[56] References Cited

U.S. PATENT DOCUMENTS

| 3,906,198 | 9/1975 | November | 73/61.1 R |
| 3,952,592 | 4/1976 | Schlatter et al. | 73/194 R |
| 4,055,082 | 10/1977 | November | 73/194 R |
| 4,059,744 | 11/1977 | Elderton | 235/92 FL |

Primary Examiner—Joseph M. Thesz
Attorney, Agent, or Firm—A. Donald Stolzy

[57] ABSTRACT

A net oil computer including a mean density electric current source that alternately supplies all of or a portion of water density and oil density electric currents with the differences between the mean and water currents and between the mean and oil currents alternately charging and discharging a capacitor between two different voltage levels or vice versa. A bistable circuit switches the capacitor to charge and discharge when the capacitor voltage reaches the respective two different levels. One or both of the capacitor charging and discharging periods may then be used to gate turbinemeter pulses, the number of which is proportional to total oil flow and/or total water flow in a pipeline.

2 Claims, 4 Drawing Figures

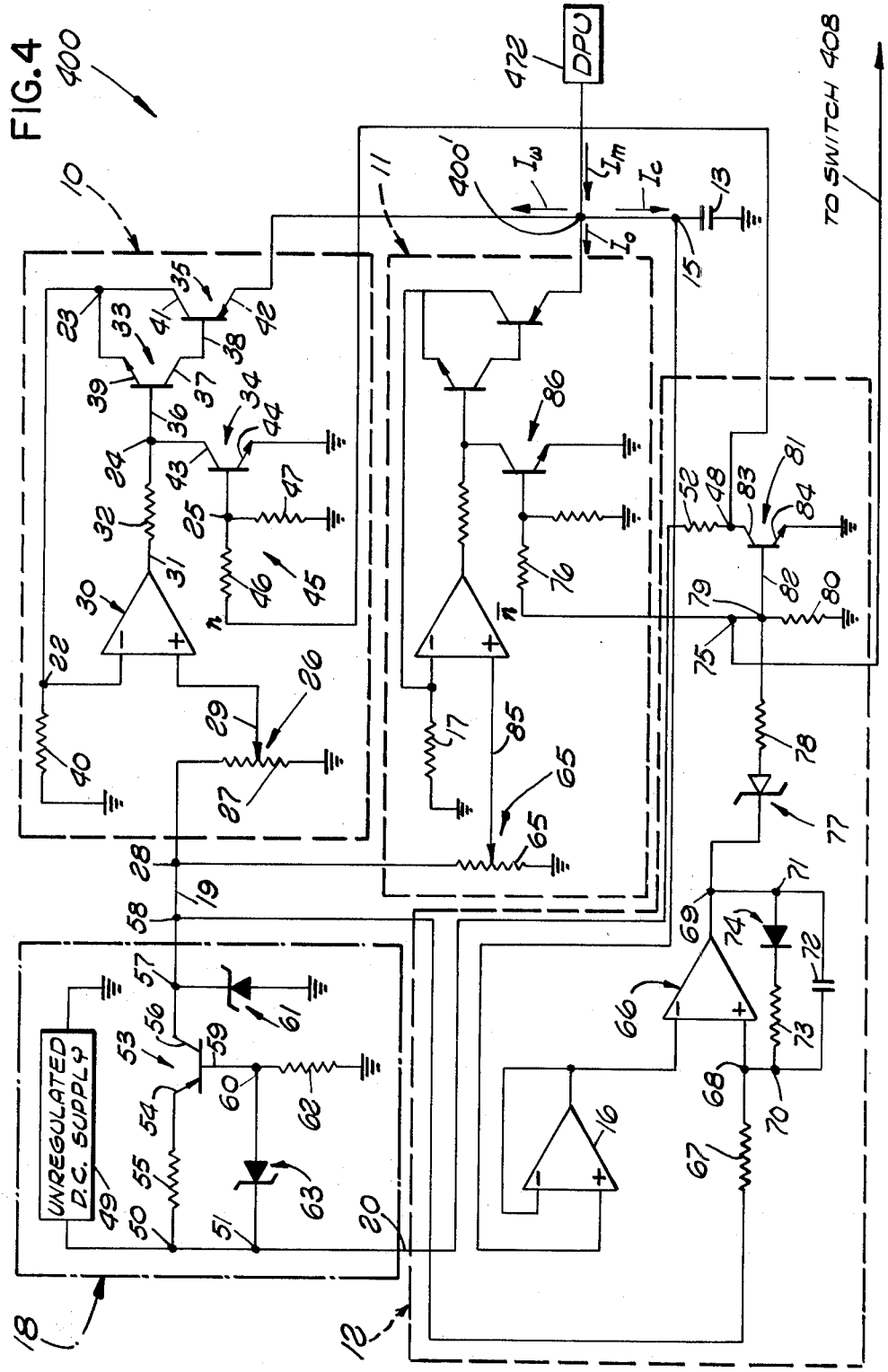

FLOW DETECTION SYSTEM

BACKGROUND OF THE INVENTION

This invention relates to a system for determining the proportionate volumetric amount of one or both of two fluids in a mixture thereof, and more particularly to a net oil computer or the like.

PRIOR ART STATEMENT

It is old in the art to utilize a ramp generator with constant voltage inputs in a net oil computer. For example, see U.S. Pat. Nos. 3,842,655; 3,385,108; and 3,544,909, respectively issued Oct. 22, 1974, May 28, 1968, and Dec. 1, 1970.

It is also old in the art to utilize a differential pressure unit (DPU) to obtain a mean density analog. See U.S. Pat. No. 4,059,744 issued Nov. 22, 1977, referred to hereinafter as patent (A), and the references cited therein.

It is old in the art to produce a D.C. electric current analog of differential pressure. See U.S. Pat. No. 3,518,886 issued July 7, 1970, referred to hereinafter as patent (B).

Further, it is old in the art to express mathematically the percent by volume or proportionality of oil and/or water in an oil and water mixture. See U.S. Pat. No. 4,055,082 issued Oct. 25, 1977, referred to hereinafter as patent (C), and the prior art statement therein.

Prior art net oil computers are considerably complicated in construction.

SUMMARY OF THE INVENTION

In accordance with the system of the present invention, the above-described and other disadvantages of the prior art are overcome by developing two switching periods, the ratio of one to the sum being proportional to the percent by volume of a corresponding one of two fluids in a mixture thereof.

BRIEF DESCRIPTION OF THE DRAWINGS

In the accompanying drawings which illustrate an exemplary embodiment of the present invention:

FIG. 4 is a schematic diagram of the gate generator shown in FIG. 2.

DESCRIPTION OF THE PREFERRED EMBODIMENT

Figure 1:
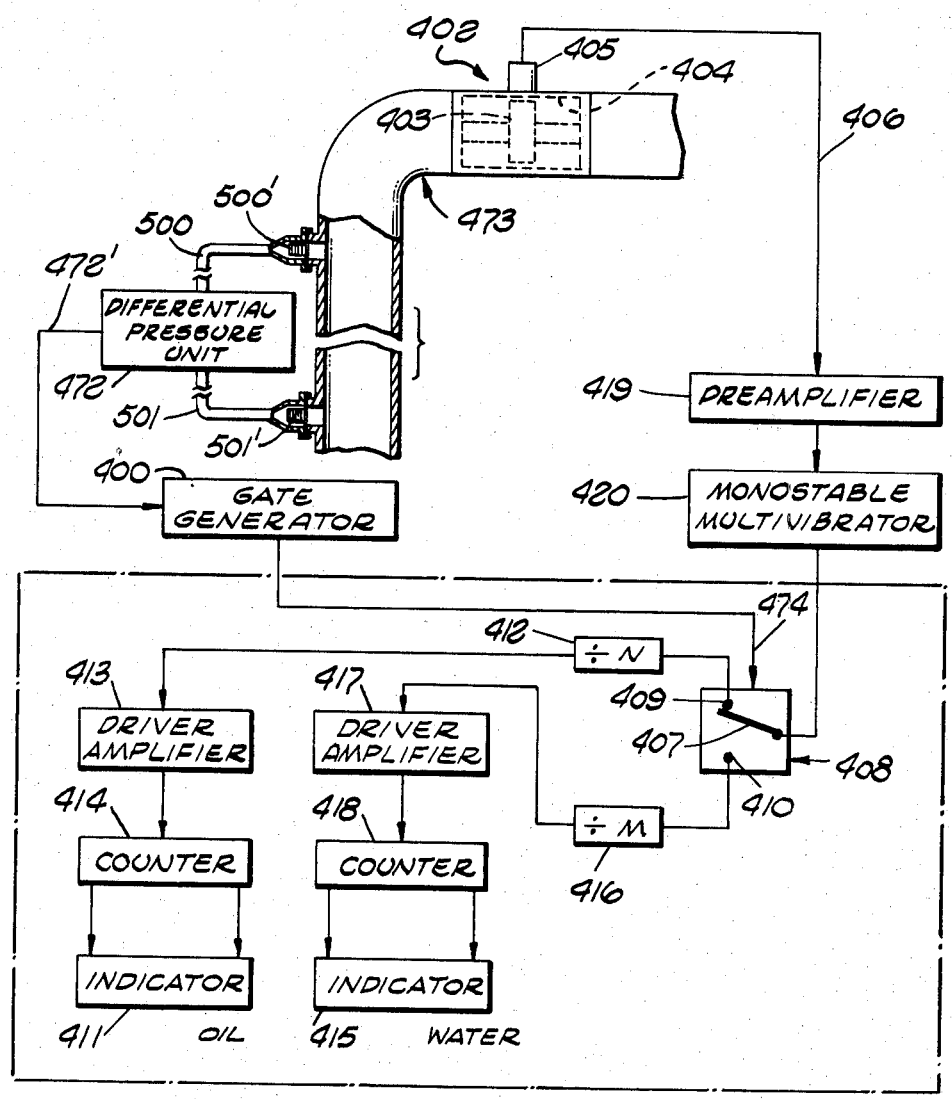
FIG. 1 is a diagrammatic view of one embodiment of the net oil computer of the present invention.

A net oil computer constructed in accordance with the present invention is shown in FIG. 1. The embodiment of FIG. 1 can produce numbers of pulses proportionate to percent oil and/or percent water by volume. The computer of FIG. 1 has components mounted in or on a pipeline 473. One component is a conventional differential pressure unit (DPU) 472 having inlet tubes 500 and 501. DPU 472 may be identical to that disclosed in patent (B), if desired. DPU 472 produces an output current $I_m$ in output lead 472' proportional to the mean density of the oil and water mixture flowing in pipeline 473. Tubes 500 and 501 are maintained at different elevations. Bellows 500' and 501' separate fill fluid on the left of bellows 500' and 501' from the oil and water mixture on the right of the bellows 500' and 501'.

A gate generator 400 is connected from lead 472' over a lead 474 to a switch 408.

In FIG. 1, the net oil computer also includes a turbine flowmeter 402 which has a turbine bladed rotor 403 and a stator 404. Flowmeter 402 also has a magnetic or other pickup 405. Flowmeter 402 is entirely conventional and produces a pulse train on an output lead 406. The pulse repetition frequency (PRF) of the pulses on lead 406 is directly proportional to the volume flow rate within pipeline 473. In other words, the flow rate is the rate of volume flow of both oil and water combined, that is the mixture thereof. The output of flowmeter 402 is impressed on the pole 407 of switch 408, which may be a conventional electronic switch. Switch 408 is located in an output circuit 471. Switch 408 may, however, be a relay or otherwise. Switch 408 has contacts 409 and 410. Contact 409 is connected to a conventional indicator 411 via a conventional divider 412, a conventional driver amplifier 413 and a conventional counter 414. Contact 410 is connected to a conventional indicator 415 through a conventional divider 416, a conventional driver amplifier 417 and a conventional counter 418.

Flowmeter 402 is connected to switch pole 407 through a conventional preamplifier 419 and a conventional monostable multivibrator 420.

Switch 408 is operated by gate generator 400. The turbine rotor 403 is immersed in the mixture of oil and water flowing in pipeline 473.

Scalers 412 and 416 may be employed to cause indicators 411 and 415 to read in volume units.

Figure 2:
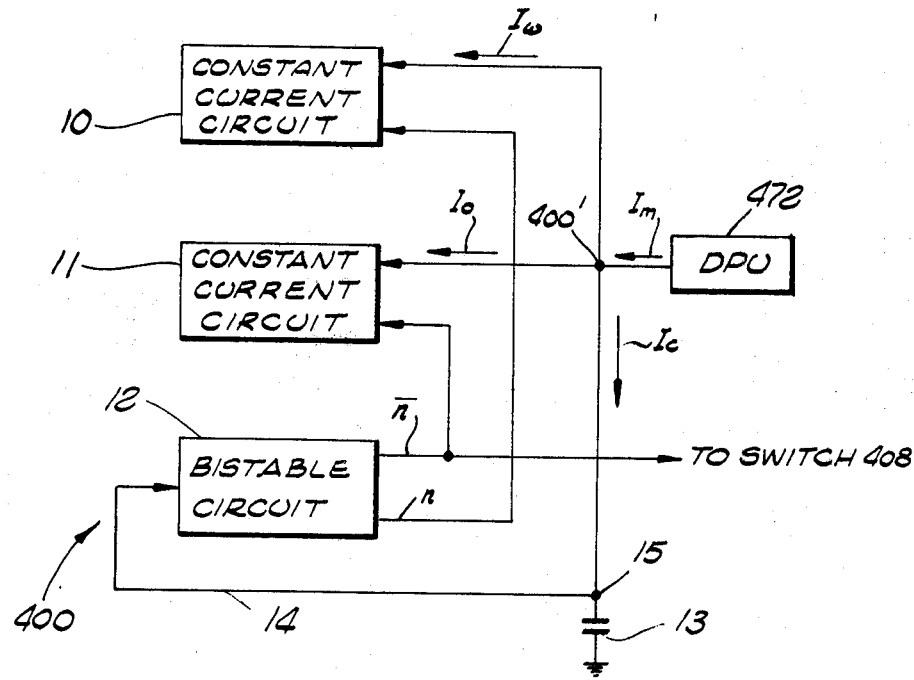
FIG. 2 is a block diagram of a gate generator shown in FIG. 1.

Everything shown in FIG. 2 is included in gate generator 400 except that the showing of DPU 472 has been repeated.

Otherwise, constant current circuits 10 and 11 are provided with a bistable circuit 12. A capacitor 13 is also provided.

The input to circuit 12 is over a lead 14 from a junction 15 which carries the voltage of capacitor 13. Lead 14 is connected to a conventional high impedance input of a conventional amplifier 16 (FIG. 4). Lead 14 therefore carries negligible current.

Figure 3:
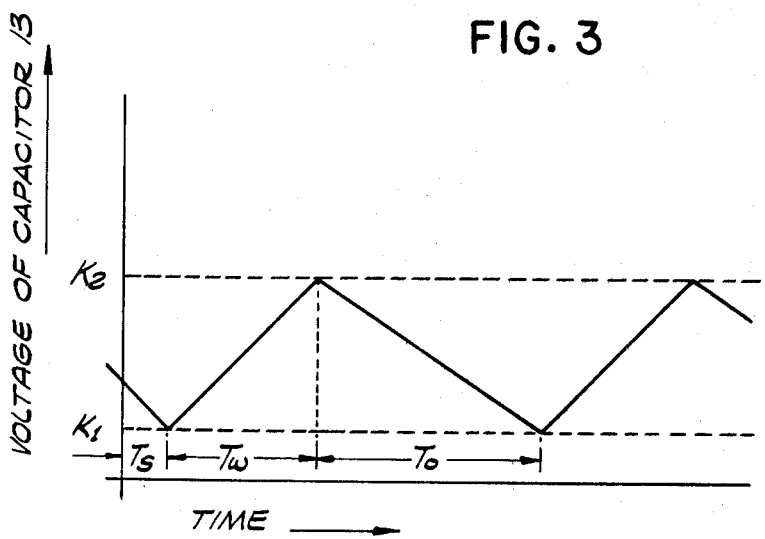
FIG. 3 is a graph of the voltage across a capacitor shown in FIG. 2.

In FIG. 2, circuit 12 is essentially a dual comparator that is bistable. When n is high, $\bar{n}$ is low, and vice versa. Circuit 12 changes state when junction reaches voltage $K_1$ and when it reaches $K_2$ (FIG. 3).

Circuit 10 admits only current $I_w$ when the magnitude of n is appropriate. Circuit 11 admits current $I_o$ when $\bar{n}$ is appropriate. Currents $I_w$ and $I_o$ flow alternately but never simultaneously. Current $I_m$ flows all the time.

When $I_w$ flows, the lead which otherwise carries $I_o$ is essentially open circuited. Conversely, when $I_o$ flows, the lead which otherwise carries $I_w$ is essentially open circuited.

Currents $I_o$ and $I_w$ represent currents proportional to oil density and water density. The oil and water may be separated in a conventional manner by a centrifuge or otherwise, and their densities measured.

$I_o$ and $I_w$ are adjusted by moving wipers 85 and 29, respectively, of potentiometers 64 and 26, respectively, shown in FIG. 4.

Currents $I_o$ and $I_w$ may be considered constant, if desired. Alternatively, a resistance temperature probe or thermistor may be employed in pipeline 473 and used in series with or parallel with a resistor 17 in FIG. 4, or in parallel with a resistor in series with resistor 17 or otherwise.

Over period $T_w+T_o$ in FIG. 3, $I_o$, $I_w$ and $I_m$ will all be effectively constant. Current $I_w$ will not normally vary to any extent with respect to time. Current $I_m$ will vary some, but insignificantly over the period $T_w+T_o$.

In FIG. 2, when the $I_o$ lead is "disconnected" by $\bar{n}$, the voltage swing of capacitor 13, $(K_2-K_1)$ as is well known, is $$\frac{1}{C} \int_{T_s}^{T_s + T_w} I_{cw} dt \quad (1)$$

or $$\frac{T_w I_{cw}}{C} = K_2 - K_1 \quad (2)$$

where C is the capacitance of capacitor 13, and $$I_c = I_{cw} = I_m - I_w \quad (3)$$

$$T_w = \frac{C(K_2 - K_1)}{I_m - I_w} \quad (4)$$

Similarly, during $T_o$ $$T_o = \frac{C(K_2 - K_1)}{I_o - I_m} \quad (5)$$

Note in (4) that if $T_w$ is positive, always $$K_2 > K_1 \quad (6)$$

$$I_m > I_w \quad (7)$$

In (5), if $T_o$ is always positive, always $$K_2 > K_1 \quad (8)$$

$$I_o > I_w \quad (9)$$

Thus, always $$I_o > I_w \quad (10)$$

If (and it can be)

$$I_w > I_o \quad (11)$$

all subscripts w may be substituted for all subscripts o, and vice versa.

That is, oil density may be greater than or less than water density.

It is known that the percent by volume of oil $p_o$ and percent by volume of water $p_w$ have the following proportionalities—see patent (C):

$$p_o \propto \frac{d_m - d_w}{d_o - d_w} \quad (12)$$

$$p_w \propto \frac{d_o - d_m}{d_o - d_w} \quad (13)$$

where
 $d_m$ is mean density,
 $d_w$ is water density, and
 $d_o$ is oil density.
If $$I_o = K d_o \quad (14)$$

$$I_w = K d_w \quad (15)$$

$$I_m = K d_m \quad (16)$$

where K is a constant, then $$p_o \propto \frac{I_m - I_w}{I_o - I_w} \quad (17)$$

and $$p_w \propto \frac{I_o - I_m}{I_o - I_w} \quad (18)$$

In FIG. 2, either lead $\bar{n}$ or n may be connected to switch 408 (FIG. 1). However, there remains to be proved:

$$p_o \propto \frac{T_o}{T_o + T_w} \quad (19)$$

and $$p_w \propto \frac{T_w}{T_o + T_w} \quad (20)$$

PROOF

From (4) and (5)

$$T_w + T_o = \frac{C(K_2 - K_1)(I_o - I_w)}{(I_m - I_w)(I_o - I_m)} \quad (21)$$

$$\frac{T_o}{T_o + T_w} = \frac{C(K_2 - K_1)}{I_o - I_m} \times \frac{(I_m - I_w)(I_o - I_m)}{C(K_2 - K_1)(I_o - I_w)} \quad (22)$$

$$\frac{T_o}{T_o + T_w} = \frac{I_m - I_w}{I_o - I_w} \quad (23)$$

Combining (17) and (23)

$$p_o \propto \frac{T_o}{T_o + T_w} \quad (24)$$

q.e.d.

See (19).
A similar proof exists for (20).

OPERATION

DPU 472 in FIG. 1 produces an output current $I_m$ in lead 472' proportional to mean density $d_m$. This current is supplied to a junction 400' (FIG. 2). The sum of the currents to junction 400' is zero when $I_o = 0$ thus $$I_m - I_w I_{cw} = 0 \quad (25)$$

where $I_c = I_{cw}$, the capacitor current, and $$I_{cw} = I_m - I_w \quad (26)$$

where $I_w$ is directly proportional to water density $d_w$.

The capacitor voltage then increases in a straight line from $K_1$ to $K_2$ over period $T_w$ (FIG. 3), the capacitor voltage having a slope $$I_{cw}/C \quad (27)$$

Thus $$\frac{I_{cw}}{C} = \frac{K_2 - K_1}{T_w} \quad (28)$$

-continued $$T_w = \frac{C(K_2 - K_1)}{I_{cw}} \quad (29)$$

From (25) and (29)

$$T_w = \frac{C(K_2 - K_1)}{I_m - I_w} \quad (30)$$

Compare (30) with (4). See also (5).

Pole 407 of switch 408 (FIG. 1) is in the position shown when, for example, current $I_o$ flows to circuit 11 (FIG. 2). Pole 407 is in its other position when $I_w$ flows. Either n or n̄ may operate switch 408 depending upon which is high or low when switch pole 407 is in the position shown to deliver turbinemeter oil pulses.

Current $I_o$ is directly proportional to oil density $d_o$. Switch 408 gates a number of pulses to oil indicator 411 proportional to the percent by volume of oil, and the balance to water indicator 415. Water indicator 415 thus shows the total volume of water flow and oil indicator 411 shows the total volume of oil flow. Except for DPU 472 being a current source, and except for the fact that no temperature compensation is provided in FIG. 1, the net oil computer of FIG. 1 may operate in the same manner as that disclosed in patent (A).

In FIG. 2, $I_w$ flows when $I_o = O$. In the former case, the capacitor charges, $I_m > I_w$. The slope of the capacitor voltage versus time curve is thus positive during time period $T_w$ (FIG. 3). In the latter case, the slope is negative ($I_o > I_m$) over period $T_o$ because $I_c$ is negative. Thus, to compute time $T_o$ so that $T_o$ is positive $$T_o = \frac{C(K_2 - K_1)}{I_o - I_m} \quad (31)$$

See (5). During discharge, the capacitor current is $$I_c = -I_{co} \quad (32)$$

The sum of the currents to junction 400' (FIG. 2) again is zero, and $$I_m - I_o - I_{co} = O \quad (33)$$

$$I_{co} = I_o - I_m \quad (34)$$

Gate generator 400 in FIGS. 1 and 2 is again shown in FIG. 4. A source 18 is provided in FIG. 4 which may be entirely conventional. Source 18 supplies unregulated and regulated D. C. voltages over leads 19 and 20, respectively. Circuits 10, 11 and 12 are also provided.

Circuits 10 and 11 may be identical except maybe for circuit values. Thus, only circuit 10 will be described in detail.

Junctions are provided at 22, 23, 24 and 25.

Potentiometer 26 is provided having a winding 27 connected from a junction 28 to ground, and a wiper 29 connected to the noninverting input of a differential amplifier 30.

Amplifier 30 has an output lead 31 connected to junction 24 through a resistor 32.

NPN transistors are provided at 33 and 34. A PNP transistor is provided at 35.

Transistor 33 has a base 36 connected from junction 24, a collector 37 connected from a base 38 of transistor 35, and an emitter 39 connected to junction 23.

Junctions 22 and 23 are connected together.

A resistor 40 is connected from junction 22 to ground. Amplifier 30 has an inverting input connected from junction 22.

Transistor 35 has a collector 41 connected from junction 23, and an emitter 42 connected to junction 400'.

Transistor 34 has a collector 43 connected from junction 24, and an emitter 44 connected to ground. A voltage divider 45 has serially connected legs 45 and 47 extending, respectively, to junction 25 from a junction 48, in circuit 12 and from ground.

Source 18 includes an unregulated supply 49 connected through junctions 50 and 51 to junction 48 through a resistor 52 in circuit 12.

Source 18 has a PNP transistor 53 including an emitter 54 connected from junction 50 via a resistor 55, a collector 56 connected through a junction 57 to junctions 58 and 28, and a base 59 connected to a junction 60.

A zener diode 61 is connected from junction 57 to ground. A resistor 62 is connected from junction 60 to ground. Another zener 63 is connected between junctions 51 and 60.

Circuit 11 has potentiometer 64 which is similar to potentiometer 26 in circuit 10. Potentiometer 64 has a winding 65 connected from junction 28 to ground as before.

In circuit 12, amplifier 16 is a unity gain voltage amplifier having a noninverting input connected from junction 15 and an output connected to its inverting input and to the inverting input.

Amplifier 66 has a noninverting input connected from junction 58 through a resistor 67 and a junction 68.

The output of amplifier 66 is connected to a junction 69. Junctions 70 and 71 are respectively connected from junctions 68 and 69. A capacitor 72 is connected between junctions 70 and 71. A resistor 73 and a diode 74 are connected in series between junctions 70 and 71.

Junction 75 is connected to switch 408 and to a resistor 76 in circuit 11 corresponding to resistor 46 in circuit 10.

A zener 77 and a resistor 78 are connected in series from junction 69 through junctions 79 and 75.

A resistor 80 is connected from junction 79 to ground.

An NPN transistor is provided at 81 including a base 82 connected from junction 79, a collector 83 connected from junction 48, and an emitter 84 connected to ground.

Bistable circuit 12 may be any conventional bistable circuit with two comparators or otherwise. Rapid switching with hysteresis may be employed.

For rapid switching note positive feedback resistor 73 in circuit 12. At $K_2$, zener 77 becomes non-conductive; transistor 81 then is immediately cut off, and junctions 79 and 75 are essentially at ground. Junction 48 is the complement of junction 75. When amplifier 66 saturates high, the noninverting input is above the potential of junction 58. When amplifier 66 saturates low, the current through resistor 67 is zero in magnitude.

Potentiometer 64 has wiper 85 similar to wiper 29. The settings of wipers 85 and 29 determine the magnitudes of $I_o$ and $I_w$, respectively.

It is well known that a circuit similar to circuit 10 will drive the inverting input voltage of amplifier 30 essentially to a potential that is equal to that of wiper 29. This means that the current through resistor 40 is constant and is essentially equal to $I_w$. The inverting and noninverting input impedances of amplifier 30 are conventionally extremely high. Thus, effectively no current flows from junction 22 to the inverting input of amplifier 30, and $I_w$ flows from junction 23 to junction 22 and thence through resistor 40 to ground.

The base current of transistor 33 is negligible.

Control of transistors 34 and 86 alternately cause $I_w$ and $I_o$ to flow while $I_o$ and $I_w$, respectively, are alternately zero.

The phrase "constant current circuit" is hereby defined for use herein and in the claims to means a circuit which is actuable to receive a finite constant current and which is deactuable to receive a negligible or zero current, wherein the finite current is effectively constant and predetermined whether or not corrected for a change in oil and/or water temperature. Thus, the maximum change of temperature with respect to time is negligible over the period $T_w + T_o$.

What is claimed is:

1. A flow detection system, said system comprising: conduit means to contain the flow of a mixture of first and second fluids having different densities; flow means connected with said conduit means to produce pulses at a rate proportional to the volume flow rate of said mixture; mean density means having an output lead and being connected with said conduit means to produce an electric current $I_m$ in said output lead proportional to the mean density of said mixture; first and second constant current circuits connected from said mean density means output lead and having respective first and second gating leads; a capacitor of capacitance C connected from said mean density means output lead to a point of reference potential; a bistable circuit having first and second output leads and adapted to generate first and second bilevel signals on said first and second leads thereof, respectively, said bistable circuit first and second leads being connected to said first and second gating leads, respectively, to cause the current $I_w$ to the first circuit to be approximately constant and proportional to the density of said first fluid, and, at the same time, to cause the current to said second circuit to be zero, said bistable circuit causing the current $I_o$ to said second circuit to be approximately constant and proportional to the density of said second fluid, and, at the same time, to cause the current to said first circuit to be zero, said bistable circuit being constructed to change states upon the arrival of said capacitor at voltages $K_1$ and $K_2$ of different respective magnitudes; pulse receiving means; and a switch connected from said flow means and having a control lead, said switch being actuable over said control lead to deliver a portion of said pulses over a period of time to said pulse receiving means, one of said bistable circuit output leads being connected to said switch control lead to close said switch for said period, said period being one of the following two periods:

$$T_w = \frac{C(K_2 - K_1)}{I_m - I_w}$$
$$T_o = \frac{C(K_2 - K_1)}{I_o - I_m}$$

2. The invention as defined in claim 1, wherein said receiving means includes a pulse counter and an indicator connected therefrom to display total flow of water in units of volume.

* * * * *